(12) United States Patent
Case et al.

(10) Patent No.: US 7,670,366 B2
(45) Date of Patent: Mar. 2, 2010

(54) INTRALUMINAL SUPPORT DEVICE WITH GRAFT

(75) Inventors: Brian C. Case, Bloomington, IN (US); Jacob A. Flagle, Bloomington, IN (US); Ram H. Paul, Bloomington, IN (US); Andrew K. Hoffa, Bloomington, IN (US); Michael L. Garrison, Indianapolis, IN (US); Joseph F. Obermiller, West Lafayette, IN (US)

(73) Assignee: Cook Incorporated, Bloomington, IN (US)

( * ) Notice: Subject to any disclaimer, the term of this patent is extended or adjusted under 35 U.S.C. 154(b) by 995 days.

(21) Appl. No.: 10/820,918

(22) Filed: Apr. 8, 2004

(65) Prior Publication Data

US 2004/0225348 A1 Nov. 11, 2004

Related U.S. Application Data

(60) Provisional application No. 60/461,339, filed on Apr. 8, 2003.

(51) Int. Cl.
*A61F 2/06* (2006.01)

(52) U.S. Cl. .................................................. 623/1.13

(58) Field of Classification Search .............. 623/1.13, 623/1.14, 1.24, 1.26, 2.12–2.19, 23.68, 23.7
See application file for complete search history.

(56) References Cited

U.S. PATENT DOCUMENTS

| | | | |
|---|---|---|---|
| 4,580,568 A | | 4/1986 | Gianturco |
| 4,725,274 A | | 2/1988 | Lane et al. |
| 5,562,728 A | * | 10/1996 | Lazarus et al. ............. 623/1.14 |
| 5,562,729 A | | 10/1996 | Purdy et al. |
| 6,077,296 A | | 6/2000 | Shokoohi et al. |
| 6,129,755 A | * | 10/2000 | Mathis et al. ............. 623/1.15 |
| 6,231,598 B1 | | 5/2001 | Berry et al. |
| 6,287,330 B1 | * | 9/2001 | Johansson et al. .......... 623/1.13 |
| 6,287,335 B1 | | 9/2001 | Drasler et al. |
| 6,299,635 B1 | | 10/2001 | Frantzen |
| 6,464,720 B2 | | 10/2002 | Boatman et al. |
| 6,494,909 B2 | | 12/2002 | Greenhalgh |
| 6,508,833 B2 | | 1/2003 | Pavcnik et al. |
| 7,452,371 B2 | * | 11/2008 | Pavcnik et al. ............. 623/1.24 |
| 2001/0039450 A1 | | 11/2001 | Pavcnik et al. |
| 2002/0002400 A1 | * | 1/2002 | Drasler et al. ............. 623/1.15 |
| 2002/0120338 A1 | * | 8/2002 | Boyer et al. ............. 623/17.19 |
| 2002/0138135 A1 | * | 9/2002 | Duerig et al. ............. 623/1.24 |
| 2002/0177890 A1 | * | 11/2002 | Lenker ...................... 623/1.12 |
| 2003/0176912 A1 | * | 9/2003 | Chuter et al. ............. 623/1.13 |
| 2003/0236568 A1 | | 12/2003 | Hojeibane et al. |
| 2004/0019374 A1 | | 1/2004 | Hojeibane et al. |
| 2004/0093070 A1 | | 5/2004 | Hojeibane et al. |
| 2004/0225348 A1 | * | 11/2004 | Case et al. ................ 623/1.15 |

(Continued)

FOREIGN PATENT DOCUMENTS

EP 0792627 A2 9/1997

(Continued)

*Primary Examiner*—Paul Prebilic
(74) *Attorney, Agent, or Firm*—Buchanan Intellectual Property Office LLC (57) ABSTRACT

Implantable medical devices comprising a support frame and a graft member attached to the support frame. The support frame can define one or more structural features that substantially prevent migration of the graft member along the support frame.

11 Claims, 10 Drawing Sheets

U.S. PATENT DOCUMENTS

2008/0103582 A1* 5/2008 Randall et al. ............. 623/1.13
2008/0249609 A1* 10/2008 Shanley .................... 623/1.16

FOREIGN PATENT DOCUMENTS

| WO | WO 98/58600 | * | 12/1998 |
| WO | WO 99/62431 | * | 12/1999 |
| WO | WO 01/66035 A2 | | 9/2001 |
| WO | WO 01/66037 A2 | | 9/2001 |
| WO | WO 02/39888 A2 | | 5/2002 |

* cited by examiner

INTRALUMINAL SUPPORT DEVICE WITH GRAFT

CROSS-REFERENCE TO RELATED APPLICATION

This application claims priority to U.S. Provisional Application Ser. No. 60/461,339, filed on Apr. 8, 2003, the entire disclosure of which is hereby incorporated into this disclosure in its entirety.

FIELD OF THE INVENTION

The invention relates to medical devices. More particularly, the invention relates to intraluminal support devices with attached graft members. Exemplary embodiments of the invention relate to intraluminal prosthetic valves, such as prosthetic venous valves.

BACKGROUND OF THE INVENTION

Many vessels in animals transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction, and quickly close upon a change in pressure, such as a transition from systole to diastole, to prevent fluid flow in a reverse direction, i.e., retrograde flow. While these natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency is present, and can lead to discomfort and possibly ulcers in the legs and ankles.

Current treatments for venous valve insufficiency include the use of compression stockings that are placed around the leg of a patient. Surgical techniques are also employed in which valves can be bypassed or replaced with autologous sections of veins with competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990's. Coronary and peripheral stents have been proven to provide a superior means of maintaining vessel patency, and have become widely accepted in the medical community. Furthermore, the use of stents has been extended to treat aneurisms and to provide occlusion devices, among other uses.

Recently, prosthetic valves have been developed that use a support frame such as a stent. Frequently, a graft member is attached to the support frame and provides a valve function to the device. For example, the graft member can be in the form of a leaflet that is attached to a stent and movable between first and second positions. In a first position, the valve is open and allows fluid flow to proceed through a vessel in a first direction, and in a second direction the valve is closed to prevent fluid flow in a second, opposite direction. An example of this type of prosthetic valve is described in commonly owned U.S. Pat. No. 6,508,833, to Pavcnik for a MULTIPLE-SIDED INTRALUMINAL MEDICAL DEVICE, which is hereby incorporated by reference in its entirety. In other examples of prosthetic valves, a tube that terminates in leaflets is attached to one or more support frames to form a valve. The leaflets open to permit fluid flow in a first direction in response to fluid pressure on one side of the leaflets, and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

Prosthetic valves are designed to replace or supplement the function of incompetent natural valves. The use of an expandable support frame in valve devices allows for the use of minimally invasive delivery devices and techniques for placement of the valves within body vessels, which will likely lower the overall cost of treatment and increase the acceptance of these medical devices by practitioners and patients alike.

The inclusion of a support frame and a valve member, such as a graft member, in a prosthetic valve device necessarily requires a connection between these components. The dynamic environment in which prosthetic valves are placed requires a connection that minimizes migration of the graft member on the support frame.

SUMMARY OF THE INVENTION

In some embodiments, the invention provides intraluminal medical devices that include structural features adapted to enable a more stable connection between the graft member and the support frame. Thus, the invention provides implantable medical devices that include a graft member attached to a support frame that defines structural features that enable a more stable connection between the graft member and the support frame. In exemplary embodiments, medical devices according to the invention provide a valve for regulating fluid flow through a body vessel. The device is particularly well suited for percutaneous delivery through a body vessel to a point of treatment, and comprises a prosthetic venous valve in an illustrative embodiment.

The prosthetic venous valves according to the invention include a support frame, such as an endoluminal stent, that has radially compressed and radially expanded configurations. The support frame can comprise any suitable support frame, including self expandable, balloon expandable, wire, tube, metal, polymeric, composite, and other types of support frames known in the art. The devices also include at least one graft member attached to the support frame. The graft member preferably provides a valve function to the device. In exemplary embodiments, the graft member comprises a valve leaflet that moves between first and second positions while remaining attached to the support frame. In the first position, the leaflet substantially blocks the lumen of the vessel, while the lumen is substantially open when the leaflet is in the second position. Thus, the leaflet permits fluid flow through the vessel in a first direction when in the first position, and substantially prevents fluid flow in a second, opposite direction when in the second position. The graft member can also be formed into other suitable valve configurations, such as a duckbill configuration, a tube or partial tube configuration, and an evertable tube configuration. The graft member can be formed of any suitable material including natural and synthetic materials. In exemplary embodiments of the invention, the graft member is formed of an Extracellular Matrix (ECM) material, such as Small Intestine Submucosa (SIS).

The graft member can be attached to the support frame in a variety of ways, such as by sutures or other suitable attachment elements. In exemplary embodiments, the support frame defines one or more structural features that provide a securement position at which the graft member can be attached to the support frame. Preferably, the structural feature is adapted to prevent migration of the graft material relative to the support frame. The type of structural feature utilized depends on the type of support frame used. For example, when a wire support frame is utilized, a loop or eyelet structure can be formed readily in the wire of the support frame. The loop or eyelet can be used as a securement position at which the graft member can be attached to the support frame by an attachment element. If, however, a tube member is used as the support frame, such as a stent cut from a solid tube of material, the formation of loops and eyelets may be difficult. Accordingly, other structural features, such as contoured struts, areas of enlarged width, barbs formed on the struts, strut projections, clips, and other structures can be used. Also, various attachment techniques, either alone or in combination with the various structural features, can be utilized for attaching the graft member to the support frame.

In other embodiments, the graft member is adhered to itself or to the support frame with agents such as tissue adhesives, cross-linkers, or natural materials such as fibrin. Also, techniques such as laser welding can be used. Furthermore, the graft member itself can define structural features that facilitate attachment to a support frame, such as a tab and corresponding slot.

A more detailed explanation of the invention is provided by the attached drawings and detailed description, which illustrate exemplary embodiments of the invention.

DETAILED DESCRIPTION OF EXEMPLARY EMBODIMENTS OF THE INVENTION

The following provides a detailed description of currently exemplary embodiments of the invention. The description is not intended to limit the invention in any manner, but rather serves to enable those skilled in the art to make and use the invention.

A medical device according to the invention provides a support frame with an attached graft member. Exemplary embodiments of the invention provide a valve for regulating fluid flow through a body vessel. Medical devices according to these embodiments include a support frame and a graft member that imparts a valve function to the device.

The support frame provides an attachment member for the graft member. A wide variety of support frames are known in the art, and any suitable support frame can be utilized. The support frame can also provide a stenting function, i.e., exert a radially outward force on the interior vessel wall, although this function is not necessary and is considered optional. By including a support frame having stenting properties, the medical devices of the invention can provide both a stenting and a valving function at a point of treatment.

The stent art provides numerous support frames acceptable for use in the invention, and any suitable stent can be used. The support frame need only provide the desired attachment member for the graft member. The specific support frame chosen will depend on numerous factors, including the vessel in which the device is being implanted, the axial length of the treatment site, the number of valves desired in the support frame, the inner diameter of the vessel, the delivery method for placing the support frame and valve, and others. Those skilled in the art can determine an appropriate support frame based on these and other factors.

The support frame can be either self-expandable or balloon expandable. A balloon expandable support frame may provide advantage to treatment sites where greater radial strength is desired. Self-expandable stents provide a relatively simple deployment at the point of treatment. Suitable support frames can also have a variety of configurations, including braided strands, helically wound strands, ring members, consecutively attached ring members, tube members, and frames cut from solid tubes.

Suitable support frames can be made from a variety of materials, and need only be biocompatible, or able to be made biocompatible, and provide the desired stenting function, if appropriate. Examples of suitable materials include, without limitation, stainless steel, nickel titanium (NiTi) alloys, e.g., nitinol, other shape memory and/or superelastic materials, cobalt-chromium alloys, natural and synthetic polymers, and composite materials. Examples of suitable polymeric materials include polypropylenes and polyethylenes. A resorbable material can also be use for the support frame. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, poly-organophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

Stainless steel and nitinol are currently considered desirable materials for use in the support frame due at least to their biocompatibility, shapeability, and well-characterized nature.

Examples of suitable support frames for use in medical devices according to the invention include those described in U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; and published United States patent application 2001/0039450 to Pavcnik et al. for an IMPLANTABLE MEDICAL DEVICE, all of which are hereby incorporated by reference in their entirety.

Figures 1, 1A:
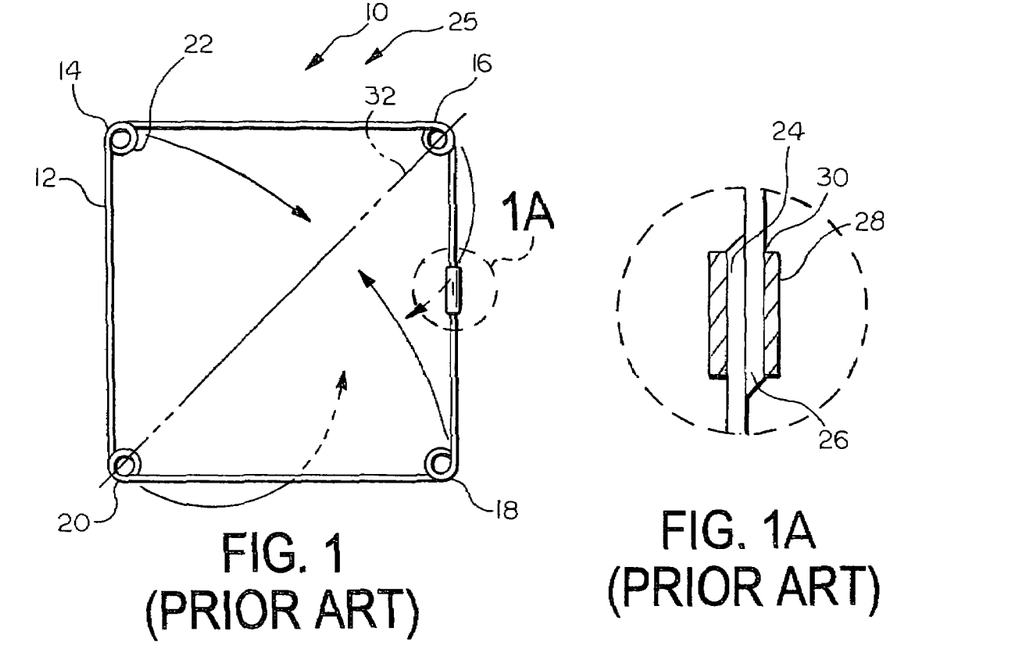
FIG. 1 is a top view of a support frame for use in medical devices according to the invention.
FIG. 1a is an enlarged partial cross sectional view of the support frame illustrated in FIG. 1.

In some embodiments of the invention, a support frame formed from wire is utilized. FIG. 1 illustrates a suitable wire support frame 10 for use in a medical device according to the invention. This support frame 10 is exemplary of suitable support frames that can be modified to include the invention. Support frame 10 is described in detail in U.S. Pat. No. 6,508,833 to Pavcnik et al. for a MULTIPLE-SIDED INTRALUMINAL MEDICAL DEVICE, which is hereby incorporated by reference in its entirety. The support frame 10 is made of resilient material, preferably metal wire formed from stainless steel or a superelastic alloy, such as nitinol. While round wire is depicted in the figure, other wire types, e.g., flat, square, triangular, D-shaped, delta-shaped, etc. may be used to form the frame. In the illustrative embodiment, the frame 10 comprises a closed circumference of a single piece of material that is formed into a device having a plurality of sides 12 interconnected by a series of bends 14, 16, 18, 20. The depicted embodiment includes four sides 12 of approximately equal length. Alternative embodiments include forming a frame into any polygonal shape, for example, a pentagon, hexagon, octagon, etc. In the embodiment of FIG. 1, each of the bends 14, 16, 18, 20 interconnecting the sides 13 comprise a coil 14 of approximately one and a quarter turns. Alternative bend embodiments include outward-projecting fillets and inward-projecting fillets comprising a series of curves. Fillets are well known in the stent art as a means to reduce stresses in bends. When using stainless steel wire, the size of the wire which should be selected depends on the size of device and the application. Wire that is too stiff can damage the vessel, not conform well to the vessel wall, and increase the profile of the device when loaded in the delivery system prior to deployment.

The single piece of material comprising the frame 10 is formed into the closed circumference by securing the first and second ends 24, 26 with an attachment mechanism 28 such as a piece of metal cannula (see FIG. 1A). The ends 24, 26 of the single piece are inserted into the cannula 28 and secured with solder 30, a weld, adhesive, or crimping to form the closed frame 10. The ends 24, 26 of the single piece can be joined directly without addition of a cannula 28, such as by soldering, welding, or other methods to join ends 24, 26. Besides joining the wire, the frame could be fabricated as a single piece of material, by stamping or cutting the frame 10 from another sheet (e.g., with a laser), fabricating from a mold, or some similar method of producing a unitary frame.

The support frame 10 depicted in FIG. 1 is shown in a first configuration 25 whereby all four bends 14, 16, 18, 20 and each of the sides 12 generally lie within a single flat plane. To resiliently reshape the frame 10 into a second configuration 35, shown in FIG. 2, the frame 10 of FIG. 1 is folded twice, first along one diagonal axis 32 with opposite bends 16 and 20 being brought into closer proximity, followed by opposite bends 14 and 18 being folded toward one another and brought into closer proximity. The second configuration 35, depicted in FIG. 2, has two opposite bends oriented at the first end 32 of the frame 10, while the other opposite bends 16, 20 are oriented at the second end 34 of the frame 10 and rotated approximately 90° with respect to bends 14 and 18 when viewed in cross-section. The medical device in the second configuration 35 can be used as a stent to maintain an open lumen 36 in a vessel 38, such as a vein, artery, or duct. The bending stresses introduced to the frame 10 by the first and second folds required to form the second configuration 35 apply force radially outward against the vessel wall 40 to hold the frame 10 in place and prevent vessel closure. Absent any significant plastic deformation occurring during folding and deployment, the second configuration 35, when not in the vessel or subject to other constraining means, will at least partially return to the first configuration 25, although some deformation can occur depending on the material used. It is also possible to plastically deform the frame 10 into the second configuration 35, such that it does not unfold when restraint is removed. This might be particularly desired if the device is made from nitinol or a superelastic alloy.

Figure 3:
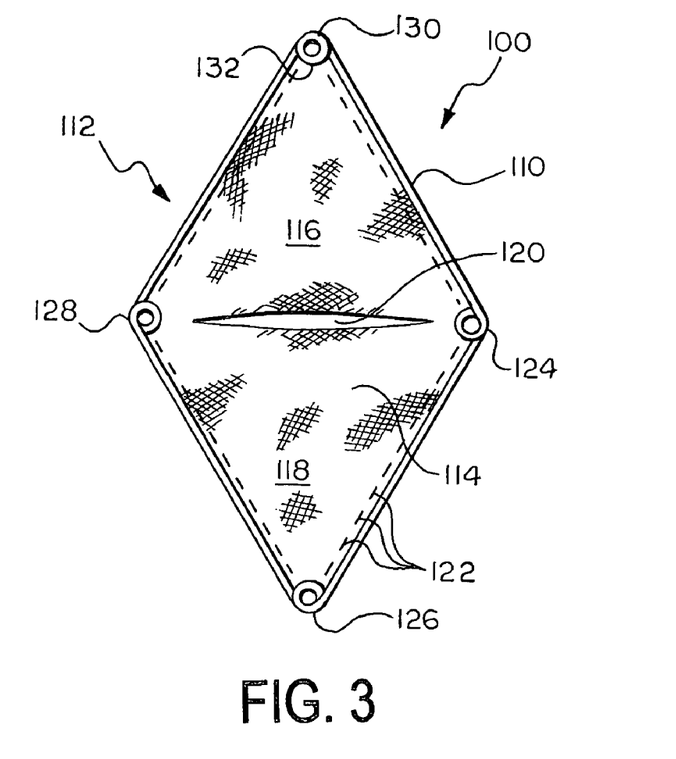
FIG. 3 is a top view of a prosthetic venous valve according to a first exemplary embodiment of the invention.

FIG. 3 illustrates a medical device 100 formed from a wire support frame 110 configured into a diamond shape 112. A graft member 114 is attached to the support frame 10 and has two leaflets 116, 118 that define a central opening 120. The graft member 114 is attached to the support frame 110 by attachment elements 122. As used herein, the term "attachment element" refers to any member that can be used to form a connection between a support frame and a graft member. Examples of suitable attachment elements include, without limitation, sutures, coils, wires, clips, rings, and other suitable members. The attachment element can comprise a separate member or can be integrally formed by the support frame or graft member. The specific attachment element chosen for a particular embodiment of the invention will depend on various considerations, including the type and configuration of the support frame and/or graft member.

Figure 2:
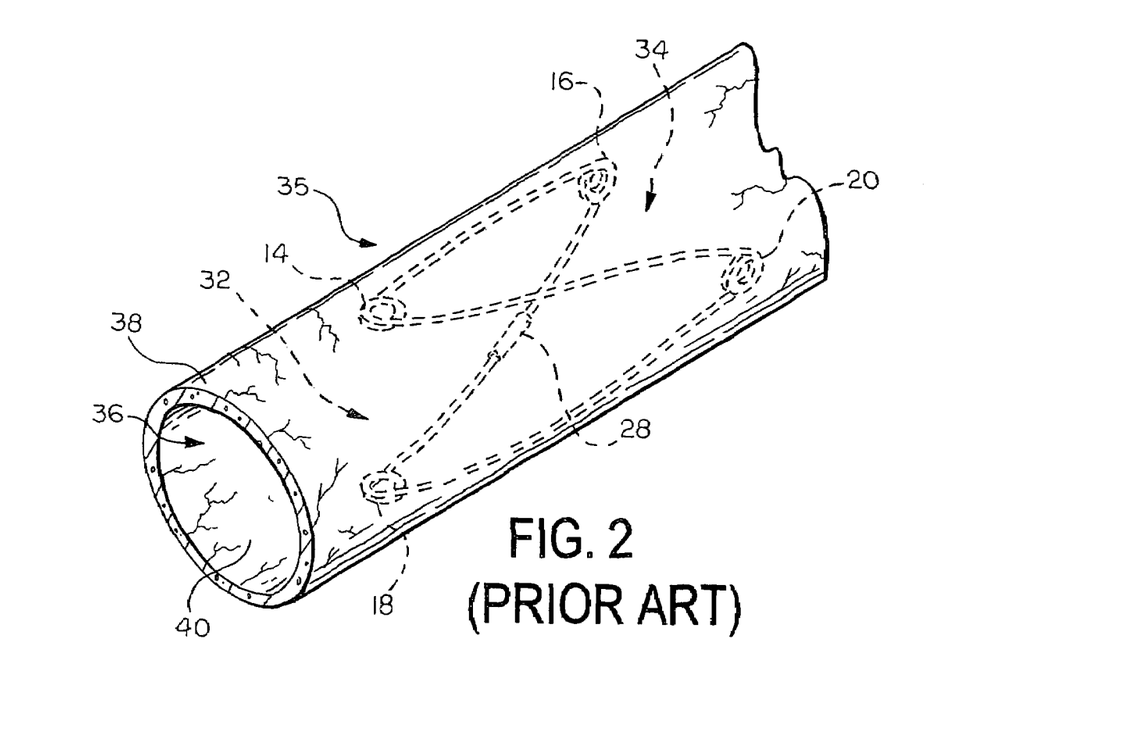
FIG. 2 is a perspective view of the support frame of FIG. 1 deployed inside a body vessel.

Similar to the embodiment illustrated in FIGS. 1 and 2, the support frame 110 illustrated in FIG. 3 includes bends 124, 126, 128 and 130 that each comprise a coil 132. The coil 132 provides an eyelet configuration in the support frame 110. As such, the coil 132 defines a structural feature in the support frame 110 to which the graft member 114 can be attached.

Figure 4:
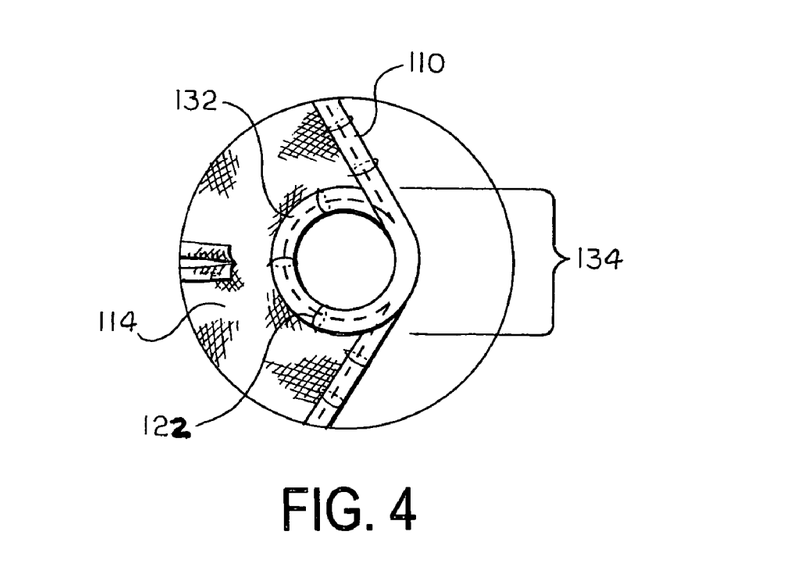
FIG. 4 is an enlarged partial view of the prosthetic venous valve illustrated in FIG. 3.

FIG. 4 illustrates a magnified view of a coil 132 in the device 100 illustrated in FIG. 3. As illustrated in FIG. 4, the graft member 114 has a notch area that receives the coil 132 and allows for the placement of attachment elements 122 around the portion of the support frame 110 in the coil 132 and through the adjacent graft member 114. In this configuration, the coil 132 provides an additional attachment point for the graft member 114. The graft member 114 is not able to migrate along the support frame 110 near the position of the coil 132 because the overlap region 134 blocks the attachment elements 122 from traveling along the support frame 110. The overlap region 134 is a length along the support frame 110 that includes at least two thicknesses of the wire member that forms the support frame 110. To further prevent migration in this area, the two portions of the support frame 110 that overlap in the overlap region 134 can be joined together by various means, such as placement of an attachment element at the overlapping portions.

Figures 5, 6:
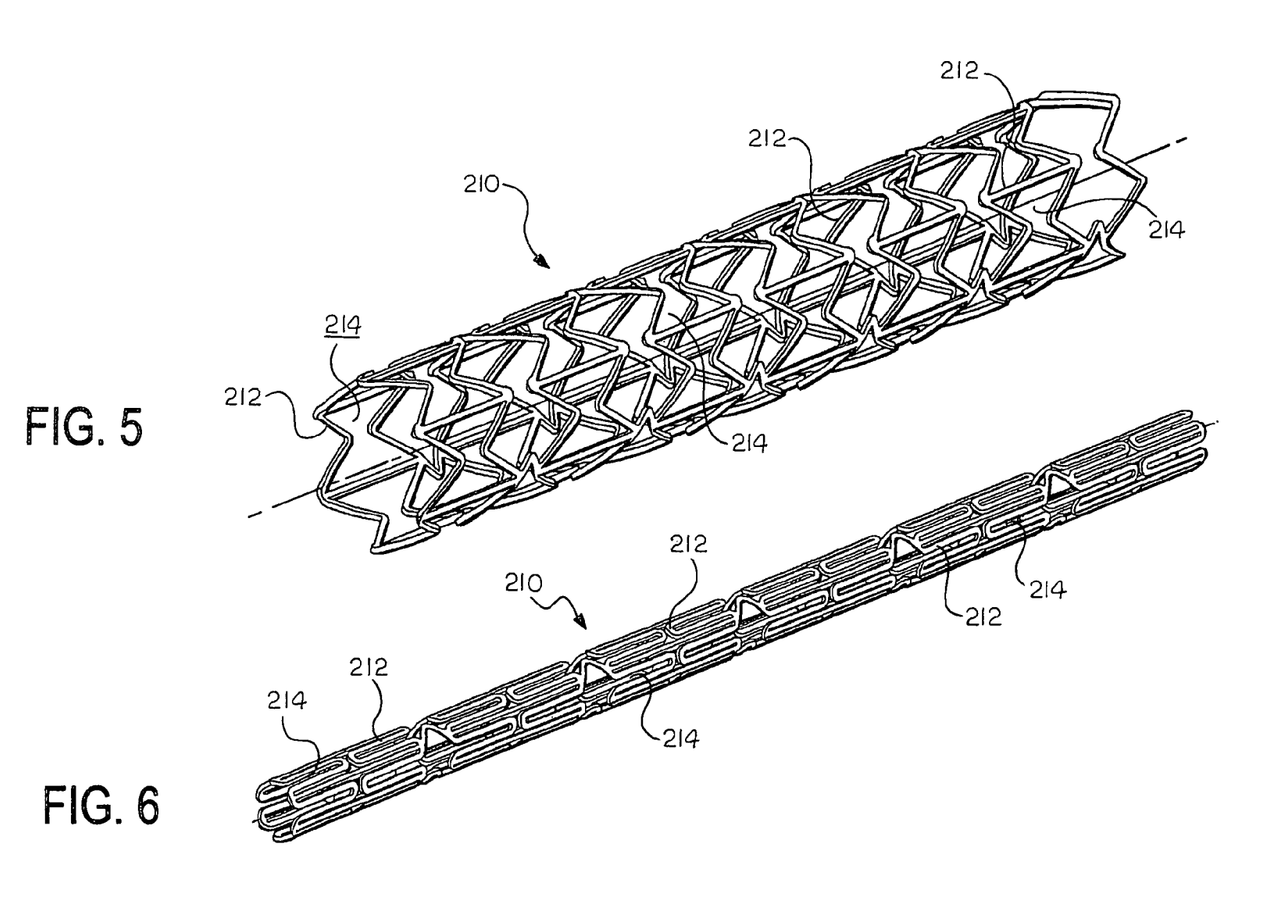
FIG. 5 is a perspective view of a support frame for use in medical devices according to the invention.
FIG. 6 is a perspective view of the support frame illustrated in FIG. 5 in a radially compressed configuration.

FIGS. 5 and 6 illustrate a second type of support frame 210 suitable for use in medical devices according to the invention. Support frame 210 is described in detail in U.S. Pat. No. 6,299,635, to Frantzen. The support frame 210 comprises a unitary member cut from a solid piece of metal tubing, such as by laser cutting. A variety of unitary support frames cut from tubes are known to those skilled in the art. Any suitable support frame of this type can be utilized in the invention. Generally, these support frames, such as the support frame 210 illustrated in FIG. 5, include a plurality of struts 212 of the tube material left after the cutting process. A plurality of open spaces 214 is formed by the removal of the material between the struts 212.

A variety of configurations of the struts 212 and open spaces 214 can be utilized. The configuration chosen will depend on numerous factors, including the size of the vessel, the desired radial strength of the stent, and the desired longitudinal flexibility of the stent. Also, as will be described more fully below, the struts 212 can be configured in a variety of manners in accordance with the invention to provide the desired attachment of the graft member to the support frame 210.

Similar to the support frame illustrated in FIGS. 1 and 2, the support frame 210 has both a radially expanded and radially compressed configuration. FIG. 6 illustrates the radially compressed configuration of the support frame 210. As best illustrated in FIG. 6, the open spaces 214 are reduced in size when the support frame is in the radially compressed configuration. Support frames cut from tube members, such as the frame 210 illustrated in FIGS. 5 and 6, are typically balloon expandable support frames.

Medical devices according to the invention include a support frame and a graft member. The graft member can be attached to the support frame in a variety of configurations. Also, the support can define structural features that are adapted to substantially prevent movement of the graft member along the struts of the support frame.

In a first series of embodiments of the invention, struts of the support frame are contoured to provide at least one non-linear segment across which a graft member can be attached. FIGS. 7 through 10 illustrate portions of medical devices in accordance with this first series of embodiments.

Figures 7, 8:
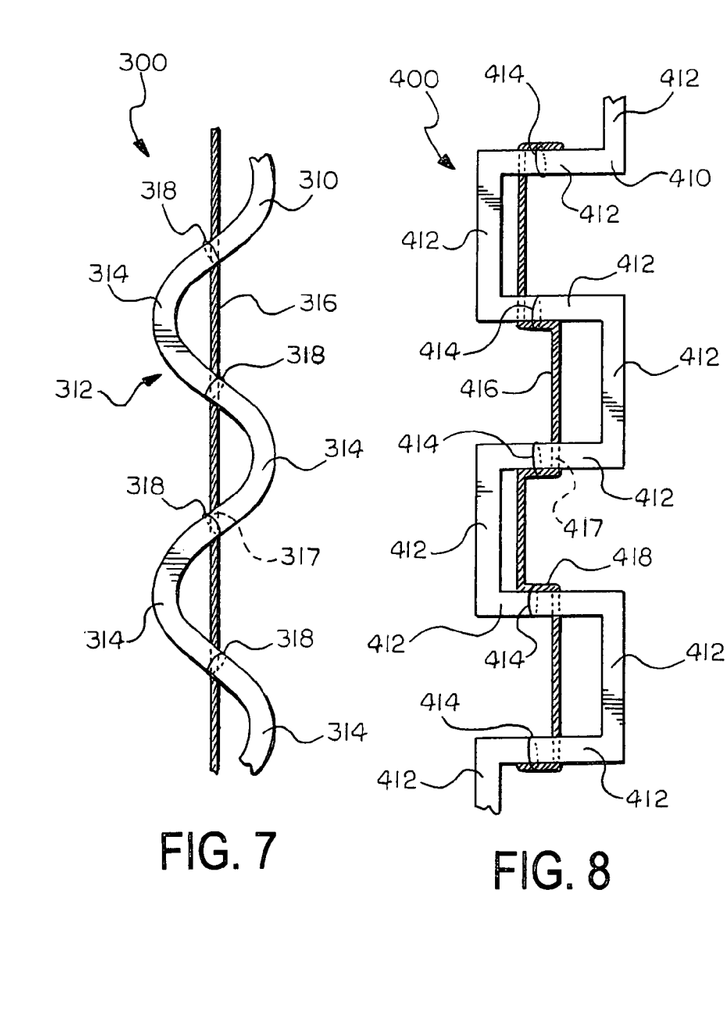
FIG. 7 is a partial view of a contoured strut for use in a medical device according to one embodiment of the invention.
FIG. 8 is a partial view of a contoured strut for use in a medical device according to another embodiment of the invention.
Figure 35:
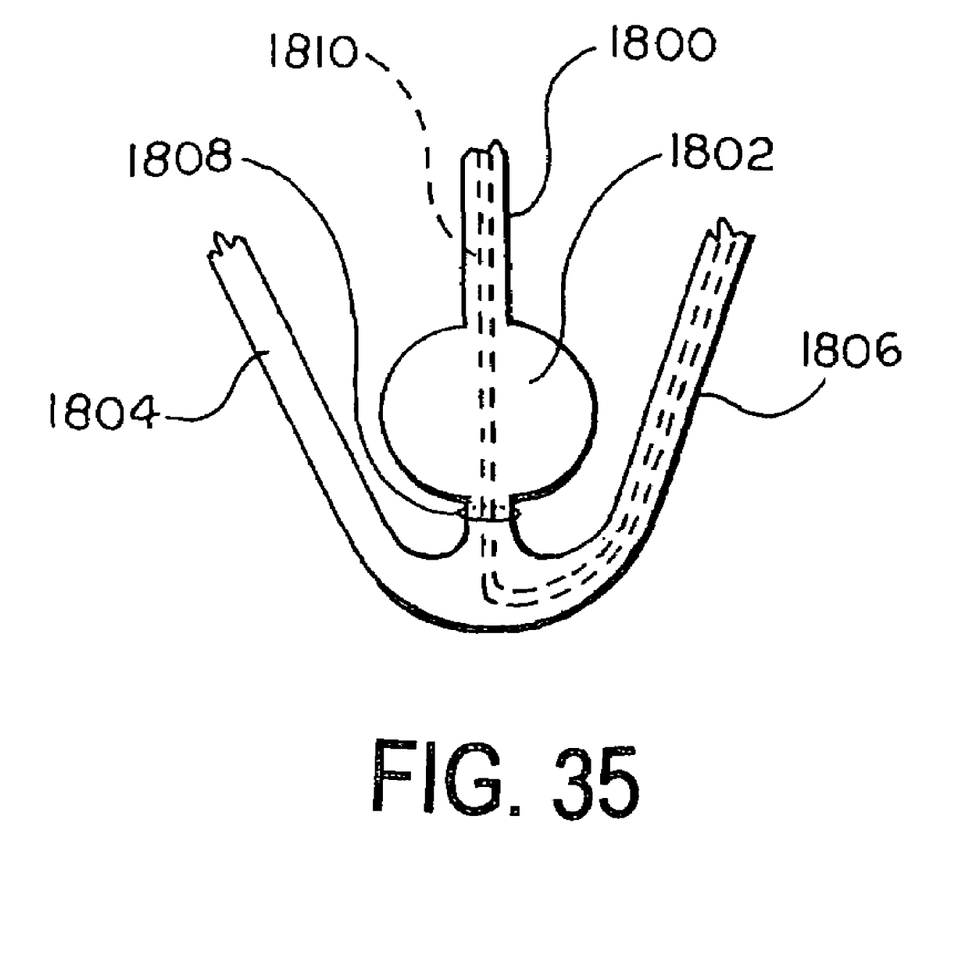
FIG. 35 is a partial view of a medical device according to another embodiment of the invention.

FIG. 7 illustrates a portion of a medical device 300 according to an embodiment of the invention. In this embodiment, a strut 310 defines a serpentine path 312 that includes a plurality of non-linear segments 314. The serpentine path 312 is defined by a single strut 310, and does not include any bend or other transition to another strut. FIG. 35 illustrates an alternate embodiment in which one strut 1800 defines a structural feature, such as enlarged region 1802, that cooperates with one or more other struts 1804, 1806 to prevent migration of an attachment element 1808 that attaches a graft member 1810 to the strut 1800. In the embodiment illustrated in FIG. 7, the graft member 316 is secured to the strut 310 by two or more attachment elements 318 that surround a circumference of the strut 310 and extend through the graft member 316. The graft member 316 is a sheet of material and an edge 317 of the graft member 316 is in contact with a surface of the strut 310. This contact can be an abutting relationship. As illustrated in the FIG. 7, an attachment element 318 can be disposed on each side of a non-linear segment 314 along the strut 310. In the illustrated embodiment, a series of attachment elements 318 are secured to the strut 310 and graft member 316 along a series of non-linear segments 314 on the strut 310. In this configuration, the graft member 316 is substantially prevented from migrating due to the curvilinear path that would need to be traveled by the attachment elements 318 for such migration to occur.

Any suitable graft member can be used in medical devices according to the invention. The graft member can comprise any suitable material for implantation in a body vessel. The graft member need only be biocompatible or be able to be made biocompatible. Examples of suitable materials for the graft member include natural materials, synthetic materials, and combinations thereof. Examples of suitable natural materials include ECMs, such as small intestine submucosa (SIS), and other bioremodellable materials, such as bovine pericardium. Other examples of ECM materials that can be used for the graft member include stomach submucosa, liver basement membrane, urinary bladder submucosa, tissue mucosa, and dura mater. Examples of suitable synthetic materials include polymeric materials, such as expanded polytetrafluoroethylene and polyurethane. ECMs are particularly well suited materials for use in the graft member, at least because of their abilities to remodel and become incorporated into adjacent tissues. These materials can provide a scaffold onto which cellular in-growth can occur, eventually allowing the material to remodel into a structure of host cells.

FIG. 8 illustrates a portion of medical device 400 according to another embodiment of the invention. In this embodiment, the strut 410 defines a plurality of angulated linear segments 412. The attachment elements 414 are preferably disposed across these angulated segments. Similar to the embodiment illustrated in FIG. 7, an edge 417 of the graft member 416 is in contact with a surface of the strut 410. In this embodiment, the graft member 416 has one or more folds 418 that are substantially coaxial with a portion of the strut 410 and provide a point at which the graft member 416 can be secured to the strut 410 by attachment element 414.

Figure 9:
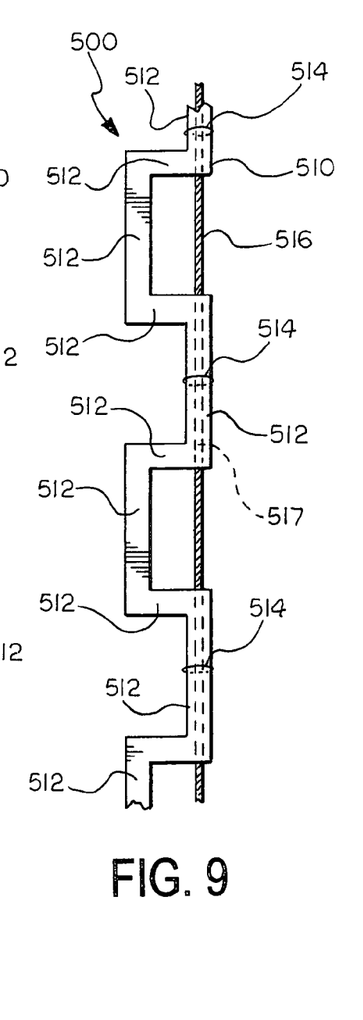
FIG. 9 is a partial view of a contoured strut for use in a medical device according to another embodiment of the invention.

FIG. 9 illustrates a portion of a medical device 500 according to another embodiment of the invention. This embodiment is similar to that illustrated in FIG. 8, except that the graft member 516 does not include folds. Thus, the strut 510 includes a plurality of angulated linear segments 512. A series of attachment elements 514 secure the graft member 516 to the strut 510. Thus, as illustrated in FIG. 9, the graft member 516 follows a substantially linear path. Also, an edge 517 of the graft member is in contact with a surface of the strut 510.

Figure 10:
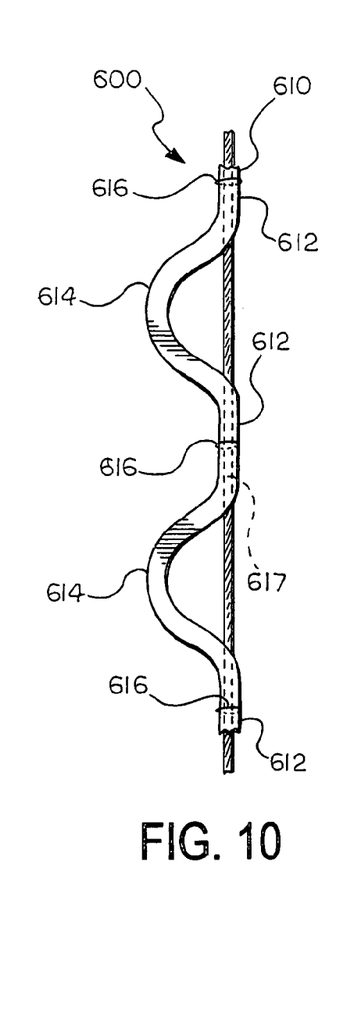
FIG. 10 is a partial view of a contoured strut for use in a medical device according to another embodiment of the invention.

FIG. 10 illustrates a portion of a medical device 600 according to another embodiment of the invention. This embodiment is similar to the embodiment illustrated in FIG. 7, except as described below. The strut 610 includes linear portions 612 disposed between adjacent curvilinear segments 614. The linear segment 612 provides an area for attachment of attachment elements 616 to the strut 610. As illustrated in FIG. 10, the curvilinear portions 614 are disposed between two linear segments 612 and provide a structural feature that substantially prevents sliding of attachment elements 616 along the strut 610. An edge 617 of the graft member 618 is in contact with a surface of the strut 610.

Figure 11:
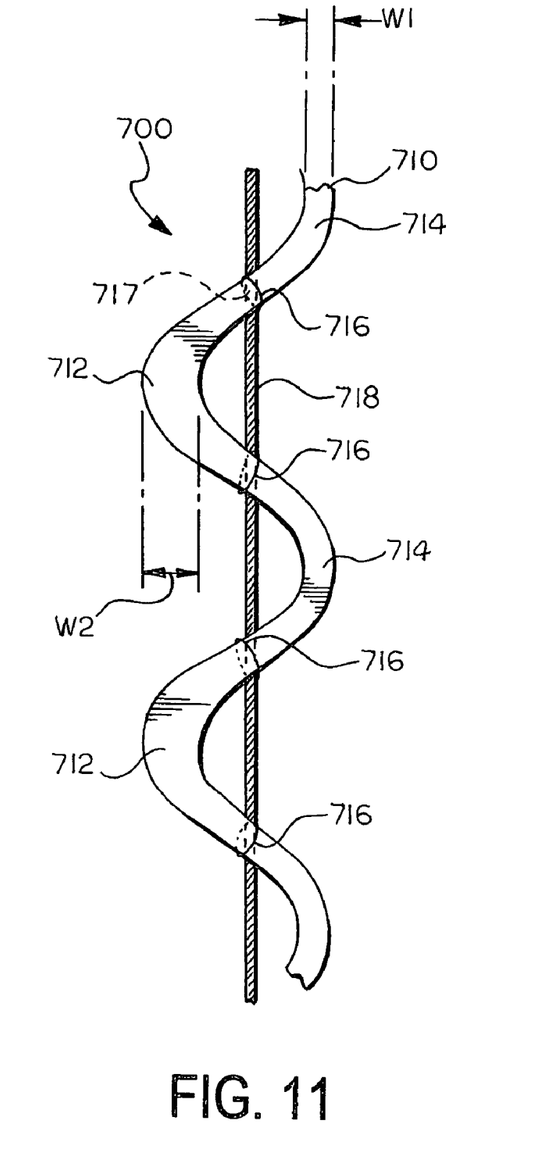
FIG. 11 is a partial view of a contoured strut having an area of increased width for use in a medical device according to another embodiment of the invention.

FIG. 11 illustrates a portion of a medical device 700 according to another embodiment of the invention. In this embodiment, the strut 710 includes a portion 712 having an increased width w2. The width w2 of the area 712 is greater than the width w1 of at least one other portion of the strut 710. As used herein, the term "width" refers to any dimension of a strut other than length, and includes a width of a substantially two dimensional strut, a thickness of a three dimensional strut, and a diameter of a strut with a substantially circular cross-sectional shape. As illustrated in FIG. 11, a portion 712 having an increased width w2 is disposed between two portions 714 of a lesser width, such as width w1. Attachment elements 716 are disposed around a circumference of the strut 710 and through the graft member 718 at a position on the strut between portions 712 and 714. The attachment elements 716 are drawn tight to the circumference of the strut 710 at these locations. Consequently, each attachment element 716 is substantially prevented from migrating towards an adjacent portion 712 of increased width w2. When two attachment elements 716 are disposed on either side of portion 712 of increased width w2, the prevention of migration is effective in both directions because migration of one attachment element 716 towards an adjacent portion 714 of lesser width w1 necessarily involves migration of the other attachment element 716 towards the portion of increased width w2, which is prevented due to the taught nature of the connection between the attachment element 716 and the strut 710. An edge 717 of the graft member 718 is in contact with a surface of the strut 710.

Figure 12:
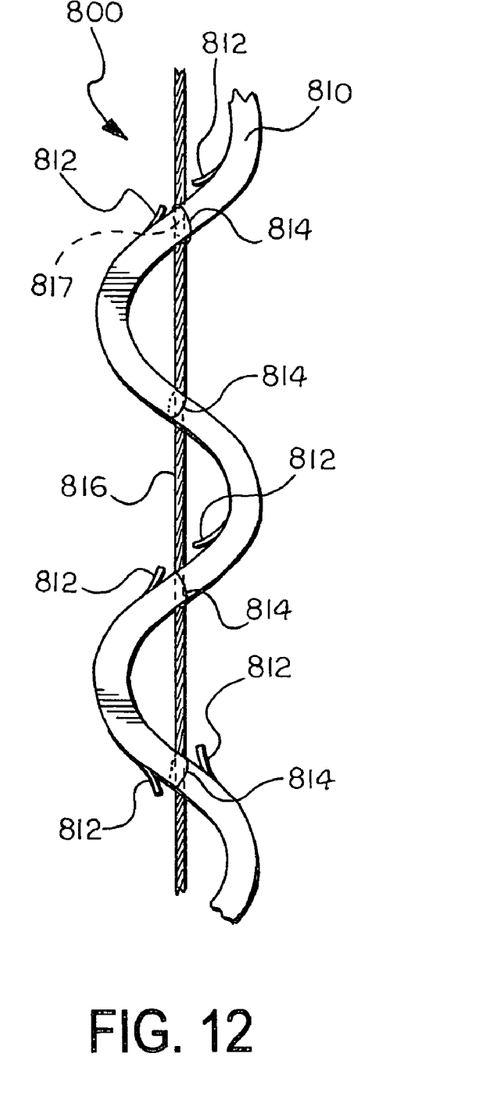
FIG. 12 is a partial view of a contoured strut defining projections for use in a medical device according to another embodiment of the invention.

FIG. 12 illustrates a portion of a device 800 according to another embodiment of the invention. In this embodiment, the strut 810 defines one or more projections 812. Attachment elements 814 are placed across a circumference of the strut 810 and through the graft member 816, adjacent one or more projections 812. An edge 817 of the graft member 818 is in contact with a surface of the strut 710. The projections 812 define stops that prevent migration of the attachment element 814 along the length of the strut 810. The projections 812 can take a variety of forms, including the barb like forms illustrated in FIG. 12, as well as bumps, nibs, and rings. Furthermore, the projections 812 can be defined by the strut 810, or alternatively can comprise separate members attached to the strut 810.

FIG. 12 illustrates three configurations of the projections 812 on the strut 810. For example, at the upper portion of FIG. 12, the strut 810 includes a single projection 812. The attachment element 814 is disposed adjacent the projection 812. In the middle portion of FIG. 12, two projections 812 are placed on a single side of the strut 810. An attachment element 814 is disposed between the projections 812. This configuration effectively captures the attachment element 814 between the projections 812. In the lower portion of FIG. 12, two projections 812 are disposed on opposite sides of the strut 810. The attachment element 814 is disposed between the opposing projections 812. In this configuration, the projections 812 define stops on each side of the attachment element 814. In medical devices according to the invention, a variety of these configurations can be used either exclusively or in any suitable combination with one another. Furthermore, as illustrated in FIG. 12, attachment elements 814 can be disposed across the strut 810 in areas that do not include any projections 812. The use of one or several projections 812 along the length of the strut 810 substantially prevents migration of the graft member 816 along the strut 810.

Figure 13:
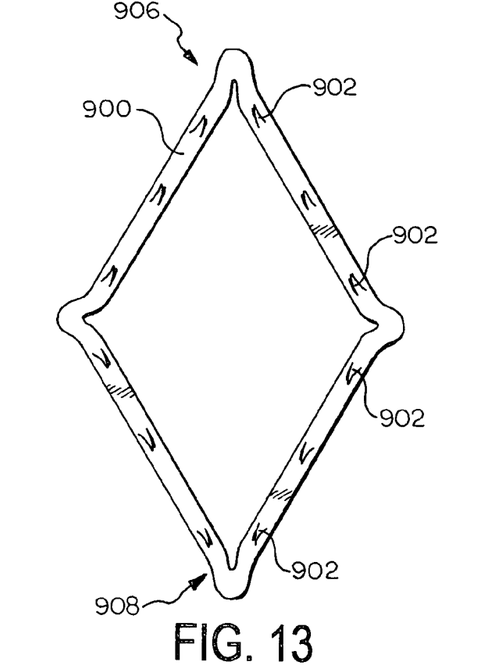
FIG. 13 is a partial view of a support frame for use in a medical device according to another embodiment of the invention.
Figure 14:
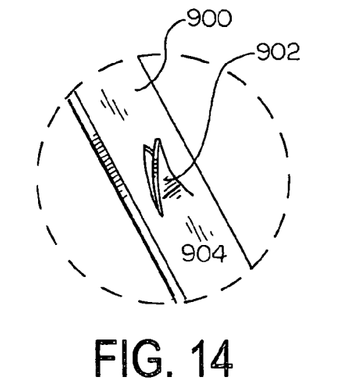
FIG. 14 is an enlarged partial view of the support frame illustrated in FIG. 13.

FIGS. 13 and 14 illustrate a support frame 900 suitable for use in medical devices according to the invention. In this embodiment, the support frame 900 defines one or more barbs 902 along its length. As illustrated in the enlarged partial view shown in FIG. 14, the barbs 902 preferably comprise pointed members extended away from the surface of the support frame 900. The pointed configuration of the barb 902 allows for piercing through an attached graft member. Each barb 902 can be formed from a portion of the material of the support frame 900, as shown in FIG. 14, or can comprise a separately attached member.

As best illustrated in FIG. 13, the barbs 902 at a first end 906 of the support frame 900 can extend in a first direction, and the barbs 902 at a second end 908 of the support frame 900 can extend in a second direction. This configuration is particularly well suited for support frames, such as the frame 900 illustrated in FIG. 13, in which the two opposing ends are brought near each other when the device is positioned within a vessel. When the two ends are brought near each other, all barbs 902 extend in the same direction, providing effective resistance to migration of an attached graft member in the opposite direction.

Figure 15:
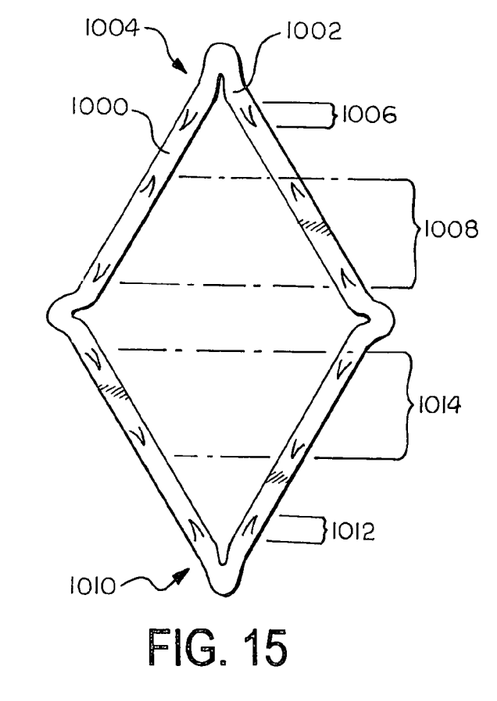
FIG. 15 is a top view of a support frame for use in medical devices according to another embodiment of the invention.

In some applications, medical devices according to the invention will be exposed to flow that occurs in both directions at different times. For example, prosthetic venous valves are exposed to both antigrade and retrograde flow continually over time. Thus, it may be desirable to provide resistance to migration of an attached graft member in both directions. FIG. 15 illustrates a support frame 1000 that includes a variety of barbs extending from its surface 1002. At a first end 1004 of the support frame 1000, a first series of barbs 1006 extend in a first direction, and a second series of barbs 1008 extend in a second, different direction, which can be a substantially opposite direction. Likewise, at a second end 1010 of the support frame, a first series of barbs 1012 extend in a first direction and a second series of barbs 1014 extend in a second, different direction. As discussed above, all of the barbs preferably comprise pointed members extending away from the surface of the support frame 1100.

Figure 16:
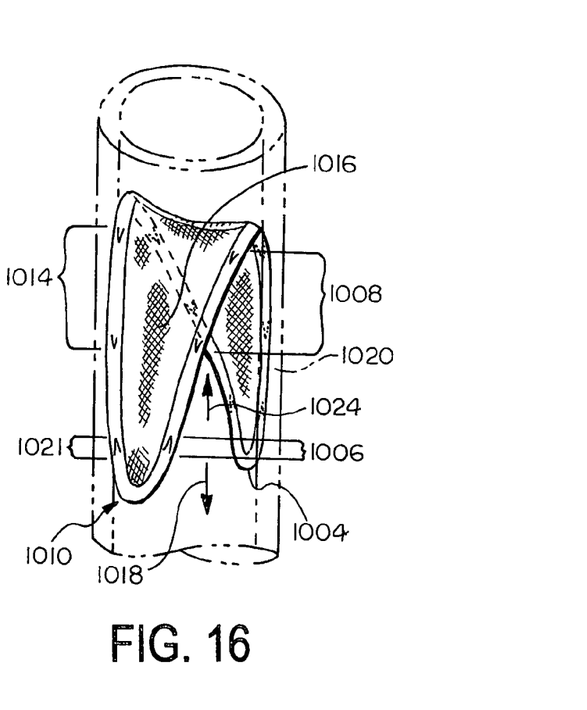
FIG. 16 is a perspective view of a medical device according to the invention positioned within a body vessel.

The first series of barbs 1006 at the first end 1004 and the first series of barbs 1012 at the second end 1010 resist migration of an attached graft member 1016 in a first direction 1018, as illustrated in FIG. 16, when the device is deployed in a vessel 1020. The second series of barbs 1008 at the first end 1004 and the second series of barbs 1014 at the second end 1010 resist migration of the graft member 1016 in a second, different direction 1024. Thus, the support frame 1000 substantially prevents migration of the graft member 1016 along the support frame 1000 in two different directions.

Figures 17, 18, 19, 20, 21:
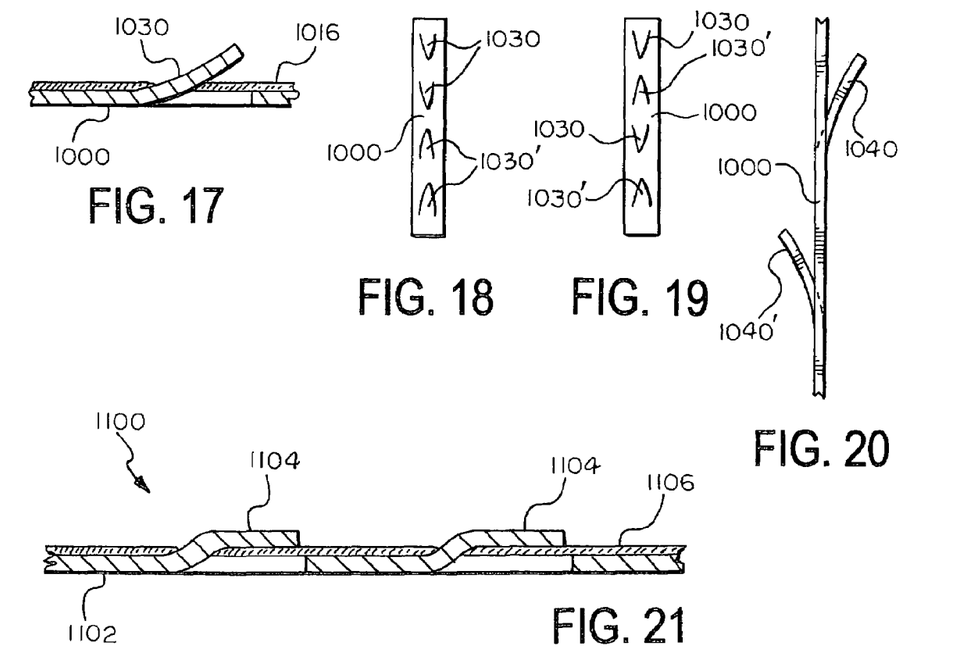
FIG. 17 is a partial cross-sectional view taken along line a-a in FIG. 16.
FIG. 18 is a schematic illustration of one configuration of barbs on a strut according to an embodiment of the invention.
FIG. 19 is a schematic illustration of one configuration of barbs on a strut according to another embodiment of the invention.
FIG. 20 is a schematic illustration of one configuration of barbs on a strut according to another embodiment of the invention.
FIG. 21 is a partial cross-sectional view of a medical device according to another embodiment of the invention.

FIG. 17 illustrates a cross-sectional view of a barb 1030 extending through the graft member 1016. By extending through the graft member 1016, the barb 1030 substantially prevents migration of the graft member 1016 along the support frame.

FIGS. 18 and 19 illustrate alternative configurations for barbs on support frame 1000. In FIGS. 18 and 19, opposing barbs 1030, 1030' are arranged on one side of support frame 1000. These configurations are particularly well-suited for use in medical devices composed of flat stock or nearly flat material.

FIG. 20 illustrates an alternative embodiment for positioning of the barbs on the support frame. In this embodiment, barbs 1040, 1040' are positioned on different sides of the support frame 1000. This is in contrast to the embodiments illustrated in FIGS. 13-19 in which the barbs are positioned on a single side of the support frame.

FIG. 21 illustrates a portion of a medical device 1100 according to another embodiment of the invention. In this embodiment, the support frame 1102 defines a plurality of projections 1104 that extend through the thickness of the graft member 1106 and along a portion of a length of the graft member 1106. In this configuration, the projections 1104 provide additional securement of the graft member 1106 to the frame by effectively clamping the graft member 1106 to the frame 1102.

Figure 22A:
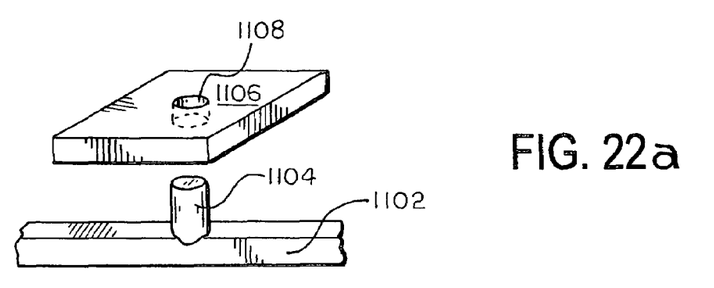
FIG. 22a is a schematic illustration of the fabrication of the medical device illustrated in FIG. 21.
Figure 22B:
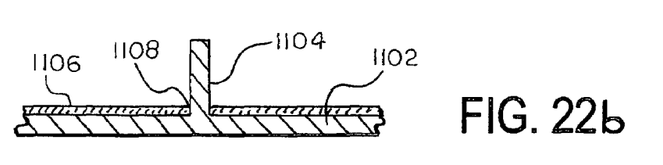
FIG. 22b is a schematic illustration of the fabrication of the medical device illustrated in FIG. 21.
Figure 22C:
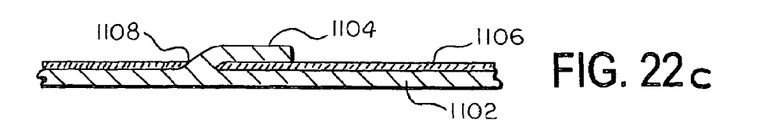
FIG. 22c is a schematic illustration of the fabrication of the medical device illustrated in FIG. 21.

FIGS. 22a, 22b, and 22c provide schematic illustrations of a fabrication process for the device 1100 illustrated in FIG. 21. First, as illustrated in FIG. 22a, a support frame 1102 includes an upstanding projection 1104. A section of graft material 1106 defining an opening 1108 is placed on the support frame 1102 such that the upstanding projection 1104 is passed through the opening 1108. FIG. 22b illustrates the intermediate product in which the graft member 1106 is positioned on the support frame 1102 and the upstanding projection 1104 extends through the opening 1108. Next, the upstanding projection 1104 is bent over a portion of the graft member 1106 so that a portion of the projection 1104 extends along a portion of a length of the graft member 1106. The graft member 1106 can be further secured to the support frame 1102 by clamping or crimping the projection 1104 against the graft member 1106 and support frame 1102, effectively capturing the graft member 1106.

FIGS. 23 through 27 illustrate portions of medical devices according to embodiments of the invention. In these embodiments, a strut 1200 defines one or more projections that define a stop for an attachment element 1202. The projections of these embodiments are similar to those illustrated in FIG. 12 and described above, except as detailed below.

Figure 23:
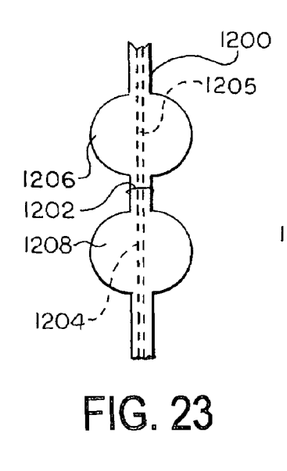
FIG. 23 is a partial cross-sectional view of a medical device according to an embodiment of the invention.
Figures 24, 25, 26:
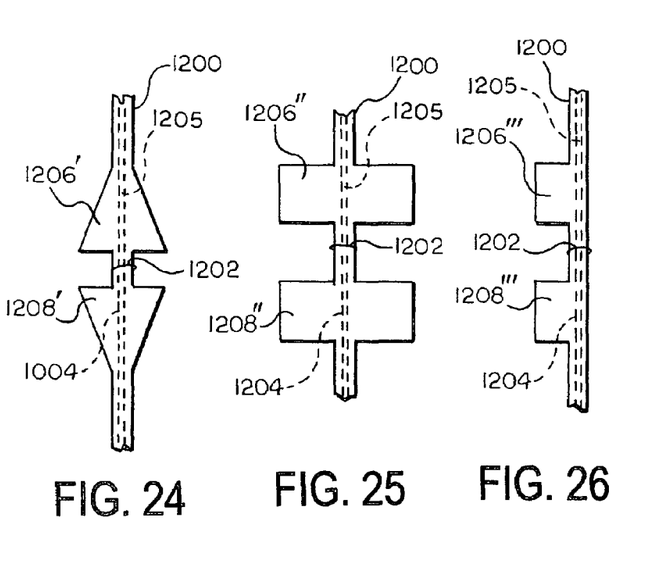
FIG. 24 is a partial cross-sectional view of a medical device according to another embodiment of the invention.
FIG. 25 is a partial cross-sectional view of a medical device according to another embodiment of the invention.
FIG. 26 is a partial cross-sectional view of a medical device according to another embodiment of the invention.

FIGS. 23 through 26 illustrate various projections that are suitable for use when it is desirable to attach a graft member 1204 to a portion of a support frame in a manner that the graft member 1204 extends substantially coplanar with the strut 1200. Also, an edge 1205 of the graft member 1204 is in contact with a surface of the strut 1200. This contact can be an abutting relationship. In FIG. 23, two projections 1206, 1208 surround a single attachment element 1202. Each of the projections 1206, 1208 define an enlarged region of the strut 1200 having a width w2 that is greater than a width w1 of a non-enlarged region of the strut 1200. This configuration essentially captures the attachment element 1202 between the enlarged regions 1206, 1208, thereby preventing migration of the graft member 1204 along the strut 1200. FIG. 24 illustrates a first alternative configuration of projections 1206', 1208'. In this configuration, the cross-sectional shape of the projections 1206', 1208' each comprise a substantially triangular shaped region defined by the strut 1200. FIG. 25 illustrates another alternative configuration of the projections 1206", 1208". In this embodiment, each of the barbs 1206", 1208" comprise a square or rectangular cross-sectional shaped area of the strut 1200. The projections 1206", 1208" extend outward from at least two sides of the strut 1200. In FIG. 26, the projections 1206''', 1208''' also comprise square or rectangular cross-sectional shaped areas of the strut 1200. In this embodiment, however, the enlarged regions 1206''', 1208''' extend outward from only one side of the strut 1200. Each of these described configurations may provide advantages in manufacturing of support frames or in assembly of the device in which the graft member 1204 is secured to the strut 1200.

Figure 27:
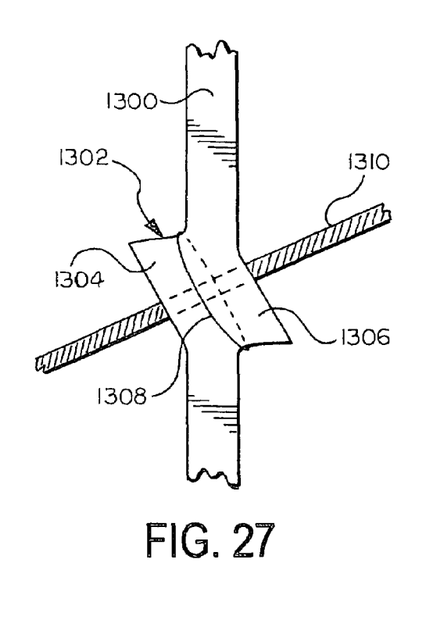
FIG. 27 is a partial cross-sectional view of a medical device according to another embodiment of the invention.

As described above, the embodiments illustrated in FIGS. 23 through 26 provide projections that are suitable for use when it is desirable to extend the graft member coplanar with a strut. In some devices, however, it may be desirable to extend the graft member at an angle with respect to a strut. FIG. 27 illustrates a strut 1300 that defines a projection 1302 that is suitable for this purpose. As illustrated in the figure, the projection 1302 comprises a first region 1304 that extends away from one side of the strut 1300 in a first direction, and a second region 1306 that extends away from a second side of the strut 1300 in a second direction. As illustrated in FIG. 27, the regions 1304, 1306 advantageously have triangular cross-sectional shapes that are substantially opposite in arrangement relative to one another. The attachment element 1308 is disposed across the projection 1302 and through the graft member 1310. The projection 1302 formed by the regions 1304, 1306 allows for placement of the attachment element 1308 at an angle to a lengthwise axis of the strut 1300, thereby allowing the graft member 1310 to be positioned at an angle with respect to the strut 1300. Also, an edge 1311 of the graft member 1310 is in contact with a surface of the strut 1300, and can be in an abutting relationship with the strut 1300. It is noted that a combination of the various projections can be used in medical devices according to the invention. For example, in a single medical device, it may be desirable to have a graft extend coplanar with a strut in one portion of the device, in which a projection such as those illustrated in FIGS. 23 through 26 would be appropriate, while having a graft member extend at an angle with respect to a strut in another portion of the device, in which a projection, such as that illustrated in FIG. 27, would be appropriate. A desirable number, configuration, and placement of the various projections used can be determined for a particular support frame in a medical device according to the invention.

Figure 28:
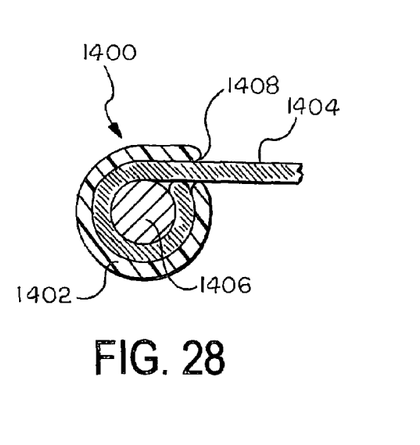
FIG. 28 is a partial cross-sectional view of a medical device according to another embodiment of the invention.

FIG. 28 illustrates a cross-sectional view of a portion of a medical device 1400 according to another embodiment of the invention. In this embodiment, a clip member 1402 is disposed around the graft member 1404 to form a snug fit between the graft member 1404 and strut 1406. The clip member 1402 is a suitable attachment element for use in embodiments of the invention. The clip member 1402 retains the graft member 1404 on the strut 1406 by this snug fit. The clip member 1402 is preferably formed of a resilient material and is force fit over the graft member 1404 and strut 1406. The clip member 1402 can take a variety of configurations. A C-shaped clip member 1402, such as that illustrated in FIG. 28, provides an opening 1408 through which the graft member 1404 and strut 1406 can be passed, while still retaining the desired snug fit. Once the clip member 1402 is positioned over the graft member 1404 and strut 1406, the clip member 1402 retains the graft member 1404 adjacent the strut 1406 by the frictional engagement of the snug fit, preventing migration of the graft member 1404 along the length of the strut 1406. Multiple clip members 1402 can be arranged at various positions on a medical device according to the invention. Also, various configurations, such as various lengths, of clip members 1402 can be used. The specific number and configuration of clip members 1402 used in any particular device will depend on various factors, such as the size of the device and the desired degree of interference fit between the strut 1406 and the graft member 1404.

To further enhance the connection between the graft member 1404 and strut 1406, additional securement means can be utilized in conjunction with the clip member 1402, such as another attachment element around a circumference of the strut 1406 and through the graft member 1404, as well as other securement means such as an adhesive disposed between the graft member 1404 and strut 1406.

Figures 29, 30, 31, 32:
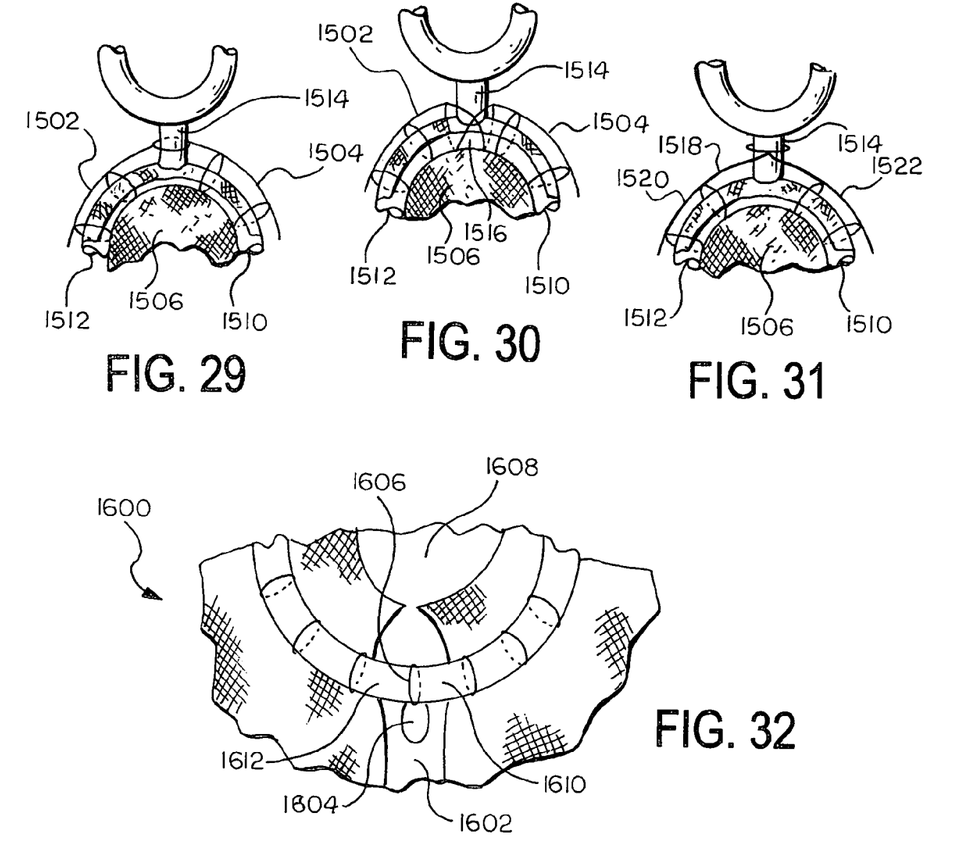
FIG. 29 is a partial view of a medical device according to another embodiment of the invention.
FIG. 30 is a top view of a medical device according to another embodiment of the invention.
FIG. 31 is a partial view of a medical device according to another embodiment of the invention.
FIG. 32 is an enlarged partial view of a medical device according to another embodiment of the invention.

Various configurations of attachment elements can be utilized to attach the graft member to the support frame. For example, FIGS. 29 through 31 illustrate various suitable arrangements that utilize sutures as the attachment elements. It is understood that other suitable attachment elements can be used in these arrangements. In FIG. 29, two individual attachment elements 1502, 1504 are passed through the graft member 1506 and around individual leg struts 1510, 1512. Also, each attachment element 1502, 1504 is tied around connecting strut 1514 that joins leg struts 1510, 1512. The embodiment illustrated in FIG. 30 is identical to that in FIG. 29, except that the attachment elements are tied around a junction area 1516 of connecting strut 1514 and the leg struts 1510, 1512. In FIG. 31, an embodiment identical to that in FIG. 29 is illustrated, except that this embodiment uses a single attachment element 1518, with portions 1520 and 1522. The use of a single attachment element 1518 eliminates one knot in the attachment element.

FIG. 32 illustrates a portion of a medical device 1600 according to an embodiment of the invention. In this embodiment, strut 1602 defines an aperture 1604. An attachment element 1606 is passed through the graft member 1608, around the leg struts 1616, 1612, and through the aperture 1606. This attachment element arrangement in combination with the structural feature of the aperture 1606 substantially prevents migration of the graft member 1608 along the leg struts 1610, 1612.

Figure 33:
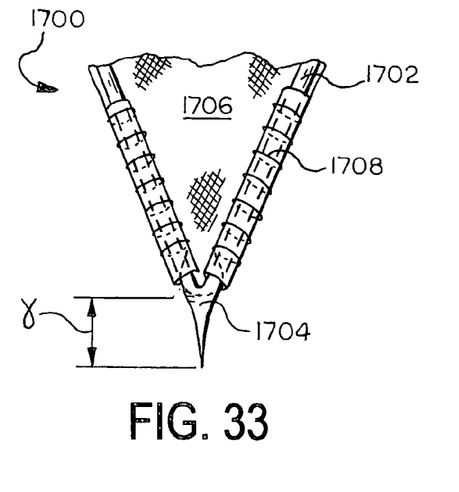
FIG. 33 is a partial view of a medical device according to another embodiment of the invention.
Figure 34:
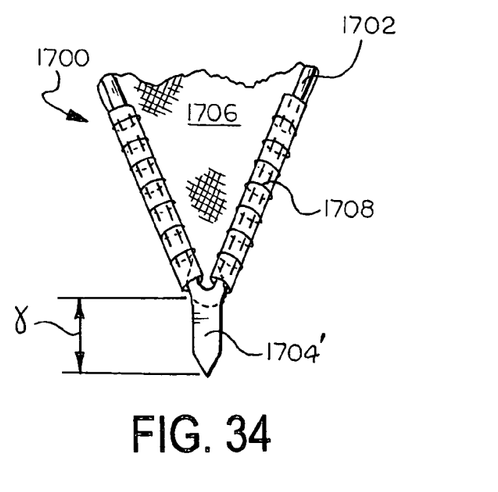
FIG. 34 is a partial view of a medical device according to another embodiment of the invention.

FIGS. 33 and 34 illustrate portions of a medical device 1700 according to another embodiment of the invention. In this embodiment, the strut 1702 defines a barb that extends away from the strut 1702. An attachment element 1708 secures the graft member 1706 to the strut 1702, and is passed behind the barb. The length y of the barb prevents the attachment element 1708 from separating from the barb as the length is greater than the slack present in the attachment element 1708, and therefore no knot is needed at the barb. The barb can comprise a member with one or more curvilinear sides, such as barb 1704 illustrated in FIG. 33, or a member with one or more linear sides, such as barb 1704' illustrated in FIG. 34. No matter the configuration, the barb advantageously includes a point 1710, which allows the barb to also provide an anchoring function to the device.

As indicated above, some medical devices, such as venous valves, are exposed to fluid flow in two opposite directions once implanted in a vessel. Accordingly, it may be necessary to include features that resist migration of the graft member in the two directions. A combination of one or more barbs disposed at one end of a device and an attachment element configuration or other feature described above can provide the desired resistance to migration in two different directions.

The foregoing description includes the best mode for practicing the invention. The description is intended only to aid in the understanding of the invention, and is not intended to limit the scope of the invention in any manner.

We claim:

1. An implantable medical device, comprising:
   an expandable support frame having a plurality of struts, at least one of the struts having a lengthwise axis and defining an undulating path forming an annular structure and having a first portion having a first width, a second portion having a second width, and a third portion having a third width, the second and third portions comprising bends in the undulating path, the second and third widths being greater than the first width and the first portion disposed between the second and third portions;
   a graft sheet having an edge extending from inner and outer surfaces thereof, the edge in direct contact with a surface of the at least one of the struts of the expandable support frame; and
   at least one attachment element disposed circumferentially around the first portion of the at least one of the struts and through a thickness of the graft sheet;
   wherein each of the first, second, and third widths being measured on an axis disposed orthogonally to and in the same plane as the lengthwise axis of the at least one of the struts;
   wherein the edge of the graft member is free of direct contact with the second and third portions of the at least one of the struts.

2. An implantable medical device according to claim 1, wherein the at least one of the struts includes a curvilinear portion and a linear portion.

3. An implantable medical device according to claim 2, wherein the linear portion comprises the first portion having the first width.

4. An implantable medical device according to claim 1, wherein the attachment element is disposed around the strut at the first portion of the strut.

5. An implantable medical device according to claim 1, wherein the attachment element is disposed around the strut and between the second and third portions of the strut.

6. An implantable medical device according to claim 1, the graft sheet further comprising an extracellular matrix material.

7. An implantable medical device according to claim 6, wherein the extracellular matrix material comprises small intestine submucosa.

8. An implantable medical device according to claim 1, wherein the graft sheet comprises a natural or synthetic polymer.

9. An implantable medical device according to claim 1, wherein the graft sheet defines a valve for regulating fluid flow through the implantable medical device.

10. An implantable medical device according to claim 9, wherein the valve is adapted to regulate fluid flow through a body vessel in which said implantable medical device is adapted to be implanted.

11. An implantable medical device according to claim 1, wherein the expandable support frame comprises a self-expandable support frame.

* * * * *